United States Patent [19]

Floyd

[11] Patent Number: 4,950,665

[45] Date of Patent: Aug. 21, 1990

[54] PHOTOTHERAPY USING METHYLENE BLUE

[75] Inventor: Robert A. Floyd, Oklahoma City, Okla.

[73] Assignee: Oklahoma Medical Research Foundation, Oklahoma City, Okla.

[21] Appl. No.: 264,088

[22] Filed: Oct. 28, 1988

[51] Int. Cl.$^5$ ............... A61K 31/54; A61K 31/33; C07D 279/18; C07D 279/00
[52] U.S. Cl. .................... 514/222.8; 544/3; 544/14; 544/32
[58] Field of Search ............ 514/222.2, 222.8; 935/1, 3; 544/3, 14, 32

[56] References Cited

PUBLICATIONS

Cadet et al., Biol. Abstr. 78 (11):80845 (1984).
Baba, et al. *Biochem. Biophys. Res. Comm.* 155(3): 1404–1411, Sep. 30, 1988.
Balzarini, J., et al., *Int. J. Cancer* 37: 451–457 (1980) to follow.
Darzynkiewics and Carter *Cancer Res.* 48, 1295–1299 (Mar. 1, 1988).
Friedmann and Brown, *Nucleic Acids Res.*, 5, 615–622 (1978).
Kornhauser, et al. *Photochem. Photobiol.* 18, 63–69 (1973).
Sastry and Gordon, *Biochim. Biophys. Acta* 129, 32–41 (1966).
Simon and Van Vunakis, *Arch. Biochem. Biphys.* 105, 197–206 (1964).
Simon, et al., *J. Mol. Biol.* 12, 50–59 (1965).
Singer and Fraenkel-Conrat *Biochim.* 5, 2446–2450 (1966).
Waskell, Al., et al., *Biochim. Biophys. Acta*, 129, 49–53 (1966).
Cadet, et al., Israel J. Chemistry 23(4), 420–429 (1983).

*Primary Examiner*—Amelia Burgess Yarbrough
*Assistant Examiner*—S. W. Zitomer
*Attorney, Agent, or Firm*—Kilpatrick & Cody

[57] ABSTRACT

The present invention is a method for using thiazin dyes, especially methylene blue, in combination with light to hydroxylate guanosine or deoxyguanosine at the C8 of the purine ring. The number of guanosines in a nucleic acid strand converted to 8-OH-deoxyguanosine (8-OH-dG) or 8-OH-guanosine (8-OH-G) can be controlled through manipulation of the concentration of methylene blue, light intensity and length of exposure, pH, and buffer strength.

The method can be used for the selective mutation or modification of either a DNA or a RNA sequence, or the protein expressed therefrom. The method can also be used in the treatment of viral infectons and in cancer. Methylene blue is FDA approved for topical, i.v., and oral administration. Viruses, bacteria, and cells undergoing rapid DNA synthesis are all inactivated by methylene blue in the presence of light or when irradiated.

6 Claims, No Drawings

PHOTOTHERAPY USING METHYLENE BLUE

BACKGROUND OF THE INVENTION

The United States government has rights in this invention by virtue of National Institutes of Health grant No. CA42854.

This invention is generally in the area of methods for modifying nucleic acids, and more specifically relates to conversion of guanine to 8-hydroxyguanine using methylene blue.

Hydroxylation of guanine in DNA to produce 8-hydroxydeoxyguanosine (8-OH-dG) may be an important factor in mutation and carcinogenesis, as reportd and described by Kasai and Nishimura, *Nucleic Acids Res.* 12, 2137-2145 (1984); *Gann.* 75, 565-566and 841-844 (1984); *Environ. Health Perspect.* 67, 111-116 (1986); Kasai, et al., *Gann.* 75, 1037-1039 (1984); *Carcinogenesis* 7, 1849-1851 (1986); Aida and Nishimura, *Mutation Res.* 192, 83-89 (1987). Kuchino, et al., *Nature (London)* 327,77-79 (1987) used synthetic oligonucleotides containing 8-hydroxydeoxyguanosine in a specific position as a template for DNA synthesis to show misreading at both the modified base and at adjacent pyrimidine bases. They observed that specific base-pairing was completely lacking at the 8-hydroxyguanosine and that incorrect bases were inserted at the adjacent pyrimidine bases. Kasai, et al., reported in *Carcinogenesis* 8(12), 1959-1961 (1987) that administration of a renal carcinogen, potassium bromate, to the rat was followed by a significant increase of 8-hydroxydeoxyguanosine in the kidney DNA, and not in non-target organ DNA.

Chemically, 8-hydroxydeoxyguanosine is generated from guanosine by the action of reagents which generate oxygen radicals such as ascorbic acid and other reducing agents, metals, polyphenols, and asbestos and by x-irradiation. Ikehara, et al., reports in *Chem. Parm. Bull.* 13(9), 1140-1142 (1965) a method wherein guanosine is heated in acetic acid with an excess of sodium acetate to synthesize 8-hydroxyguanosine.

Intracellular DNA appears to undergo repair by enzymes following formation of 8-hydroxydeoxyguanosine. This may be a naturally occurring response which has evolved to combat the effects of the many mutagens, tumor promoters, and carcinogens which cause the formation of 8-hydroxydeoxyguanosine.

Methylene blue, 3,7-Bis(dimethylamino)phenothiazin-5-ium chloride, $C_{16}H_{18}ClN_3S$, is a dark green or blue thiazin dye which was first isolated in 1876. It is FDA approved for oral administration and has been reported to be effective as an antiseptic, disinfectant, and antidote for cyanide and nitrate poisoning. For over 50 years it has been known that methylene blue is reduced by mitochondria to leukodye which is then autooxidized back to methylene blue by oxygen, yielding $H_2O_2$. This is the probable mechanism by which methylene blue, injected i.v. at a dose of 1 mg/kg body weight, is effective in the treatment of methemoglobinemia, a clinical disorder where more than 1% of the hemoglobin in the blood has been oxidized to $Fe^{3+}$. Kelner and Alexander reported in *J. Biol. Chem.* 260(28), 15168-15171 (1985), that methylene blue oxidizes glutathione directly when it is reduced by NADPH, rather than via the $H_2O_2$.

Methylene blue, in the presence of light, has been reported to damage DNA, probably by damaging or cleaving the DNA at the guanine residues. In an effort to determine the mechanism by which certain photoactive dyes react with guanosine in the presence of light, Simon and Van Vunakis, *Arch. Biochem. Biophys.* 105, 197-206 (1964), noted that the effect of several photoactive dyes, including methylene blue, and light is dependent on the concentration of the dye, as well as light wavelength and intensity, and can be correlated with uptake of oxygen and decrease in ultraviolet absorbance by guanine derivatives.

Kornhauser, et al., *Photochem. Photobiol.* 18, 63-69 (1973) attempted to characterize the changes in guanosine following exposure to methylene blue and light using thin layer chromatographic analytical techniques.

Waskell, et al., reported in *Biochim. Biophys. Acta* 129, 49-53 (1966), that extensive irradiation of polynucleotides in the presence of methylene blue causes extensive destruction of the guanosine, leaving ribose, guanidine, ribosylurea, and free urea. They postulated that the destruction of the guanosine residues was the mechanism for a previous observation by Sastry, et al., *Biochim. Biophys. Acta* 129, 42 (1966), that methylene blue and irradiation inactivate TMV-RNA. Singer and Fraenkel-Conrat, had also reported, in *Biochem.* 4, 2446-2450 (1966), that another methylene-blue type dye, thiopyronin (where the ring N is replaced by CH), and proflavin cause inactivation of TMV RNA in the presence of light.

Others have attempted to analyze the effect of methylene blue and light on DNA, but without success. Friedmann and Brown, *Nucleic Acids Res.* 5, 615-622 (1978), showed that methylene blue and light caused lesions at deoxyguanosines in DNA and that subsequent exposure to piperidine caused strand rupture. They hypothesized that cyclo-addition occurred at various positions in the purine ring, rendering the DNA susceptible to base catalysed cleavage following modification of the other nucleoside bases.

It is therefore an object of the present invention to provide a method for using methylene blue and other thiazin dyes to selectively derivatize guanosine in a controlled manner.

It is a further object of the present invention to provide a method for mutating and cleaving both DNA and RNA in a selective manner using methylene blue and other thiazin dyes.

It is another object of the present invention to provide a method for selectively inactivating viruses and cancerous cells in vivo using methylene blue and other thiazin dyes.

It is a still further object of the present invention to provide methods and compositions for the selective delivery and utilization of methylene blue and other thiazin dyes in vivo.

SUMMARY OF THE INVENTION

The present invention is a method for using thiazin dyes, especially methylene blue, in combination with light to hydroxylate guanosine or deoxyguanosine at the C8 of the purine ring. The number of guanosines in a nucleic acid strand converted to 8-OH-deoxyguanosine (8-OH-dG) or 8-OHguanosine (8-OH-G) can be controlled through manipulation of the concentration of methylene blue, light intensity and length of exposure, pH, and buffer strength. Very little, if any, other derivatives are formed.

The method can be used for the selective mutation or modification of either a DNA or a RNA sequence, or the protein expressed therefrom. 8-OH-dG and 8-OH-G do not base pair well and are especially susceptible to misreading.

The method can also be used in the treatment of viral infections and in cancer. Methylene blue is FDA approved for topical, i.v., and oral administration. Selective delivery can be achieved using systems such as liposomes for delivery to macrophages and other phagocytic cells or using biodegradable controlled release implants. Viruses, bacteria, and cells undergoing rapid DNA synthesis are all inactivated by methylene blue when irradiated with light. Treatment can be extracorporeal or by light irradiation of specific tissues using other methods. Methylene blue absorbs in the red wavelengths, i.e., approximately 670 nm, which penetrates tissue much better than other lower wavelenghts.

DETAILED DESCRIPTION OF THE INVENTION

The thiazine dye methylene blue plus light has been shown to hydroxylate both guanosine and deoxyguanosine to yield 8-OH-guanosine (8-OH-G) and 8-OH-deoxyguanosine (8-OH-dG), respectively. This can be used to selectively, and in a controlled manner, modify the guanosine in both DNA and RNA of diverse origin, including bacterial, viral and mammalian, both normal and abnormal, in solution and intracellular.

8-OH-G is used herein to refer to both 8-OH-G and 8-OH-dG unless otherwise stated. 8-OH-G produces mutations since it does not pair as well as the unaltered guanosine and because the bases adjacent to the 8-OH-G can be misread when transcribed or translated. Sequences containing the 8-OH-G are more susceptible to strand breaks so the method can also be utilized as a method for selectively cleaving and modifying sequences for insertion into vectors or sequencing.

Methylene blue is a thiazin dye. Other thiazin dyes which may be used in the present invention include compounds wherein one or both of the alkylamines, $N(CH_3)_2$, are substituted with H, $NH_2$, $NHCH_3$, $NHC_2H_5$. Other carbons may also be substituted with alkyl groups such as $CH_3$. Examples of dyes which have been tested and found to hydroxylate guanosine in the presence of light include toludine blue O, azure B, and azure A. Methylene Blue is the most active of the thiazin dyes tested at this time. Thionine, a related compound having an amine in place of the alkylamines, is not active under the test conditions. Other dyes, including eosine and Rose Bengal, are also not active under the assay conditions. Activity of the dye can be enhanced furthrr by derivatization with compounds such as antisense mRNA. Addition of enzymes such as catalase to the solution containing the dye can also be used to enhance the activity of the methylene blue plus light. Although it is not clear what the specific mechanism of action is, addition of a hydroxy radical scavenger such as mannitol does not affect the reaction.

Dye can be applied topically or systemically. Both methods of administration are approved by the Federal Drug and Food Administration for methylene blue. A procedure utilizing injection of photoactive drugs for cancer treatment is described by Edelson, et al., in *New Enqland J. Med.* 316, 297-303 (1987). In their procedure, incorporated herein by reference, the drug is crosslinked by exposure to low level ultraviolet A energy.

The dyes can be specifically delivered to cells such as macrophages using techniques such as liposome delivery. Liposomes are described in general by Gregoriadis, *Drug Carriers in Bioloqv and Medicine* Ch. 14, 287-341 (Academic Press, N.Y. 1979). Methods for making light sensitive liposomes are described by Pidgeon, et al., in *Photchem.Photobiol.* 37, 491-494 (1983). Liposome compositions are commercially available from companies such as the Liposome Company, Inc., Princeton, N.J. Release of compounds from liposomes ingested by macrophages is described by Storm, et al., in *Biochim.Biophys.Acta* 965, 136-145 (1988).

Alternatively, the dye can be delivered to a specific site for purposes such as killing of tumor cells using a controlled release polymeric implant. Polymeric implants are generally manufactured from polymers which degrade in vivo over a known period of time. Examples of useful polymers include polyanhydrides, polylactic acid, polyorthoester, and ethylene vinyl acetate. These devices are also commercially available. Alza Corporation, Palo Alto, Calif., and Nova Pharmaceuticals, Baltimore, Md, both manufacture and distribute biodegradable controlled release polymeric devices.

The present invention will be further understood with reference to the following non-limiting examples.

EXAMPLE 1

Formation of 8-hydroxyguanine in DNA using methylene blue and light.

Methylene blue plus light causes formation of 8-hydroxy-2'-deoxyguanosine (8-OHdG). The amount of 8OHdG formed in DNA by methylene blue plus light increases as a function of time in white light and as the methylene blue concentration increases. The procedure used was as follows.

2 mM Methylene blue was added to calf thymus DNA solubilized in sodium phosphate buffer (0.0935 mg DNA/ml 0.014 M Na Phosphate pH 6.8) to produce a concentration of 0.02 mM methylene blue and exposed to white light (100 watt incandescent light 11 cm from a beaker containing the sample being treated) in an ice bath. The DNA was precipitated with ethanol (400 $\mu$l 5 M NaCl in 5 ml ethanol), centrifuged at 2000 rpm for one hr at 4° C., the pellet redissolved in 250 $\mu$l Bis-Tris EDTA buffer, made 10 mM with $MgCl_2$, placed in a boiling water bath for three min then cooled rapidly, digested with DNAse I (10 $\mu$g) and endonuclease (0.6 units) overnight at 37° C. then with PDE (Calbiochem snake venom, 0.04 units) and alkaline phosphatase from calf intestine (Calbiochem, 1 unit) overnight at pH 8.0 and 37° C. to the nucleoside level, the pH dropped to 4.0 with acetic acid, the volume adjusted to 250 $\mu$l, filtered and run on HPLC. The results showed that methylene blue plus light caused formation of large levels of 8-hydroxyguanine as evidenced by a high level of 8-hydroxydeoxyguanosine in the digest.

EXAMPLE 2

Formation of 8-hydroxyguanine in RNA using methylene blue and light.

Substituting RNA for the DNA in example 1, methylene blue plus light caused formation of 8-hydroxyguanosine (8-OHG) in RNA.

EXAMPLE 3

Selective modification of deoxyguanosine to form 8-hydroxy-2-deoxyguanosine in a solution containing deoxycytosine, deoxythymine, and deoxyadenine.

When the nucleoside of adenine, cytosine, thymine, and guanine (approximately 200 nmoles each) are subjected to methylene blue (20 μl into 2.0 mls final total volume) plus light treatment (100 watt incandescent light 11 cm over solution for 15 min), using methods similar to those in example 1 only deoxyguanosine reacts based on the recovery of the nucleosides, as analyzed by HPLC.

EXAMPLE 4

Formation of 8-OH-dG in supercoiled DNA from plasmid pBR322.

Exposure of supercoiled DNA to methylene blue and light produced strand breaks in the plasmid DNA and formation of high levels of 8-OHdG. The amount of 8-OHdG present after 15 min in 0.02 mM methylene blue (100 watt incandescent bulb at 11 cm) is about 300 8OHdG/$10^5$ dG, an increase of about ten fold over the starting level (starting level was approximately $25 \times 10^5$ and the level after 30 min was approximately $560 \times 10^5$). At his level of damage, about one-half of the original supercoiled DNA remained intact.

Samples were treated for 0 min, 15 min, and 30 min, then precipitated with ethanol and NaCl addition. For restriction analysis samples were incubated in NaCl buffer at 37° C. for 2.5 hr then analyzed by gel electrophoresis.

EXAMPLE 5

Formation of 8-OH-dG in DNA of human lymphocytes using methylene blue and light.

Procedure

Methylene Blue (0.005 M Methylene Blue=18 mg) was added to a buffy coat preparation. Cell count was 8,440,000 cells/ml resuspended in BSS (11,394,000 cells/test tube). 0.1 ml of 0.5 mM methylene blue in water was added to 0.9 ml of cell suspension. The cell suspension was mixed and allowed to sit in ice 10 min. The control and sample tubes were transferred to light box. The tubes were exposed to light 15 min and then transferred to ice and into 15 ml tubes.

Cells were washed from beakers with 2 ml of saline. Cells were pelleted and the supernatants removed. 1.2 mls of lysis buffer and 0.12 ml of proteinase K incubated at 50° C. for 10 min were added to the cells. Tubes were gently mixed and put in a 57° C. water bath overnight. Lysis was complete after addition of additional enzyme and homogenization. Total volume of each lysate equaled 2.20 mls. After the cells were lysed, 3.0 mls of phenol/chloroform solution was added to each tube, which were then gently mixed. These were then centrifuged in a Sorvall at 7000 rpm for 5 min.

Two chloroform/phenol washes, and one wash with ethanol were performed, then the DNA-protein precipitated with 5 M sodium acetate and ethanol. After 4 h at −20° C., the solution was centrifuged at 9000 rpm in a Sorvall SS.34. The supernatant was removed and the precipitate washed with 70% ETOH and 100% ETOH and dried.

The pellet was resuspended in 0.5 ml H₂O, then 2.44 mls lysis buffer and proteinase K added to redigest the precipitated cells for 15 h.

The DNA was then extracted three times with chloroform/phenol then twice with chloroform. Again precipitated the suspension with 3M sodium acetate and ethanol. Centrifuged, washed and resuspended the precipitate in 0.5 ml TE. Two 2 ml of RNAse (1000 v/ml) was added and samples heated at 37° C. for 30 min, then cooled on ice. 500 ml chloroform/phenol was added to the mixture which was allowed to sit 5 min, microfuged 2 min, then extracted as before with chloroform.

40 ml of 3 M sodium acetate pH 5.5 and 400 ml of isopropanol was added and the mixture allowed to sit 5 min at room temperature before microfuging 5 min. the precipitate was washed with 70% ethanol and 100% ethanol. The pellet was dried and resuspended in 1×Bis Trizma then assayed for 8-OHdG.

The control sample contained 9.6 8-OHdG/$10^5$ dG.

The methylene blue samples contained 103 8-OHdG/$10^5$ dG.

EXAMPLE 6

Repair of 8-OH-dG lesions in DNA produced by exposure of isolated rat liver nuclei to methylene blue and light.

8-OH-dG lesions in DNA produced by exposure of isolated rat liver nuclei to methylene blue and light were repaired over a period of about an hour, as determined using methods similar to those in example one.

EXAMPLE 7

Inactivation of RNA virus R17 using methylene blue and light.

Exposure of R17 to 0.02 mM methylene blue plus light for 15 min (100 watt incandesent bulb at 11 cm) causes inactivation of R17, as assessed by its ability to form plaques on a bacterial lawn. The virus is inactivated 50% in 45 seconds by exposure to 0.05 μM methylene blue plus light.

1. Add 20 μl φ stock to 2.0 ml dilution buffer (db).
2. Dispense 0.3 ml into each of tubes A–F.
3. Add Methylene Blue to give concentrations shown in tables below.
4. Pipet 270 μl of samples to be light treated into the #1 well of a 96 well μ titer plate, corresponding to its letter label A–H.
5. Shine light through water ¼ cm deep in petri dish onto titer plate with samples for 5 minutes.
6. Add 270 μl of each sample not to be light treated to their respective #1 wells in the plate. Thus, each #1 contains 270 μl of a 1:100 dilution of stock φ, with or without MB and with or without light treatment.
7. G and H contained a 1:$10^3$ dilution of stock without BSA or supernatant, respectively, in wells #1.
8. were then titered by making serial 10x dilutions in the μ titer plate, adding 0.1 ml of selected dilution to 0.2 ml of log share x L-Blue cells (approximately $10^7$/ml) and plating 0.1 ml.

| [MB] | Light 5' | pfu |
| --- | --- | --- |
| A - | — | $3.24 \times 10^9$ |
| B - | — | $3.21 \times 10^2$ |
| C - | 20 μM | $2.73 \times 10^2$ |
| D - | 20 μM | $<3 \times 10^2$ |
| E - | 0.02 μM | $5.20 \times 10^8$ |

| [MB] | Light 5' | pfu |
|---|---|---|
| F- | 0.04 μM | $1.56 \times 10^8$ |

Methylene blue did not inhibit growth of the the bacterial lawn at the concentrations used in the R17 inactivation and titering.

Samples were also tested to determine the time of exposure of light to inactivate the virus. The procedure was as follows:

1. Add 30 μl φ (R17 phage) stock to 3 ml dilution buffer+BSA.
2. Dispense 0.3 ml into each of tubes A and B.
3. Add 60 μl of 2 μM Methylene blue to the remaining 2.4 ml φ suspension=0.05 μm MB.
4. Dispense the MB-φ suspension into the #2 well corresponding to the letter sample label A-H, in a timed sequence with light treatments as follows:

Add 0.3 ml to well H2, treat with light 0-5 min. Add 0.3 ml to well G2, treat with light 5 min-7.5 min. Add 0.3 ml to well F2, treat with light 7.5 min-9.0 min. Add 0.3 ml to well E2, treat with light 9.0 min-9.5 min. Add 0.3 ml to well D2, treat with light 9.5 min-9.9 min. Add 0.3 ml to well C2, treat with light 9.9 min-10.0 min. Add 0.3 ml to well B, no light. Add 0.3 ml to well A, no light.

Results

Bacterial plaques did not grow at either room temperature (20° C.) or at approximately 45° C., but did at 30° C. 30° C. plaque had smaller lysis rings surrounded by translucent growth.

| Time | Sample | PFU |
|---|---|---|
| none | A | $\Sigma = 2.76 \times 10^{11}$/ml |
| 0.1' | C | $= 3.3 \times 10^{11}$/ml |
| 0.5' | D | $= 5.0 \times 10^{11}$/ml |
| 1.0' | E | $= 1 \times 10^{11}$//ml |
| 2.5' | F | $= 9.1 \times 10^9$/ml |
| 5.0' | G | $= 6.93 \times 10^9$/ml |
| 10.0' | H | $= 4.35 \times 10^8$/ml |

These results demonstrate that methylene blue and light inactivated R17 under these conditions at a rate of $t_{\frac{1}{2}} = 0.8-1.0$ minutes.

The effect of methylene blue on growth following exposure to light for 5 min was then determined.

| Sample | [MB] | Light 5 min | pfu |
|---|---|---|---|
| A | None | None | $7.2 \times 10^9$ |
| B | 20 μM | None | $<3 \times 10^7$ |
| C | 20 μM | + | $4.2 \times 10^2$ |
| D | 2 μM | None | $4.8 \times 10^8$ |
| E | 2 μM | + | $3.0 \times 10^1$ |
| F | 0.2 μM | + | $3.52 \times 10^3$ |
| G | 0.04 μM | + | $1.11 \times 10^8$ |
| H | 0.02 μM | + | $5.04 \times 10^8$ |

Modifications and variations of the method to selectively and in a controlled manner hydroxylate guanosine and deoxyguanosine, and use thereof in the treatment of viral and bacterial infections and cancer, will be obvious to those skilled in the art from the foregoing detailed description. Such modifications and variations are intended to come within the scope of the appended claims.

I claim:

1. A composition for modifying nucleic acids in vivo comprising
   a thiazin dye in combination with a pharmaceutical vehicle,
   having a concentration to produce a thiazin dye dose concentration of less than or equal to 0.05 mM which is effective to selectively convert guanosine to 8-hydroxyguanosine upon exposure to non-ionizing radition.
2. The composition of claim 1 wherein the dose is effective to inactivate a virus.
3. The composition of claim 1 wherein the dose is effective to kill bacteria.
4. The composition of claim 1 wherein the dose is effective in the treatment of transformed cells.
5. The composition of claim 1 wherein the non-ionizing radiation is white light.
6. The composition of claim 1 wherein the thiazine dye is selected from the group consisting of methylene blue, toludine blue O, azure B, azure A, and combinations and derivatives thereof.

* * * * *